United States Patent [19]
Ambasz

[11] Patent Number: 5,077,855
[45] Date of Patent: Jan. 7, 1992

[54] MOTOR-DRIVEN TOOTHBRUSH

[76] Inventor: Emilio Ambasz, 295 Central Park West, New York, N.Y. 10024

[21] Appl. No.: 533,524

[22] Filed: Jun. 5, 1990

[51] Int. Cl.$^5$ .......................... A46B 13/02; A46B 7/06
[52] U.S. Cl. ...................................... 15/22.1; 15/22.2; 74/22 R
[58] Field of Search ............... 15/22.1, 22.2; 74/22 R, 74/70; 132/271, 221, 313

[56] References Cited

U.S. PATENT DOCUMENTS

| | | | |
|---|---|---|---|
| 1,517,320 | 12/1924 | Stoddart | 15/22.1 |
| 2,184,850 | 12/1939 | Schloss | 15/22.1 |
| 2,196,667 | 4/1940 | Moseley | 15/22.1 |
| 2,278,365 | 3/1942 | Daniels | 15/22.1 |
| 3,562,566 | 2/1971 | Kircher | 15/22.1 |
| 3,935,869 | 2/1976 | Reinsch | 15/22.1 |
| 4,545,087 | 10/1985 | Nahum | 15/22.1 |

FOREIGN PATENT DOCUMENTS

| | | | |
|---|---|---|---|
| 357863 | 3/1990 | European Pat. Off. | 15/22.1 |
| 3544256 | 6/1987 | Fed. Rep. of Germany | 15/22.1 |

Primary Examiner—Philip R. Coe
Assistant Examiner—Terrence R. Till
Attorney, Agent, or Firm—Brumbaugh, Graves, Donohue & Raymond

[57] ABSTRACT

A motor-driven toothbrush comprises a drive unit having a motor and a transmission that simultaneously drive a shaft in rotation and a brush head extension reciprocably in a direction parallel to the axis of the shaft. A brush unit includes a brush head coupled to the extension for lengthwise reciprocating motion on which several bristle holders, each carrying several bristle tufts, are mounted individually for pivotal movement about an axis spaced apart from and parallel to the drive shaft. A crank coupled to the drive shaft imparts pivotal movement to each bristle holder individually via a crank pin for each holder.

24 Claims, 4 Drawing Sheets

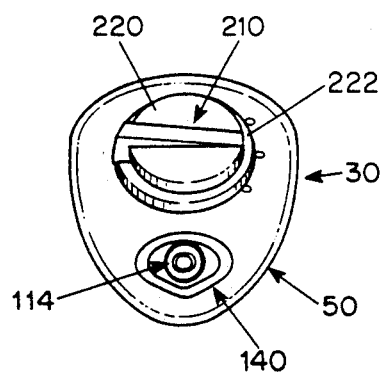
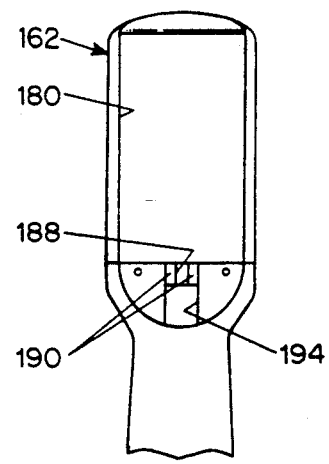
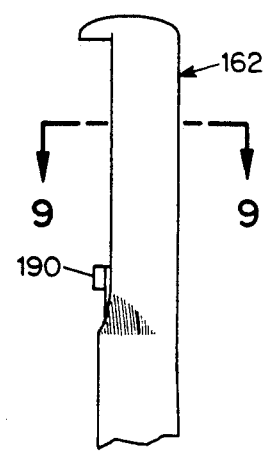
FIG. 3　　　　FIG. 6　　　　FIG. 7
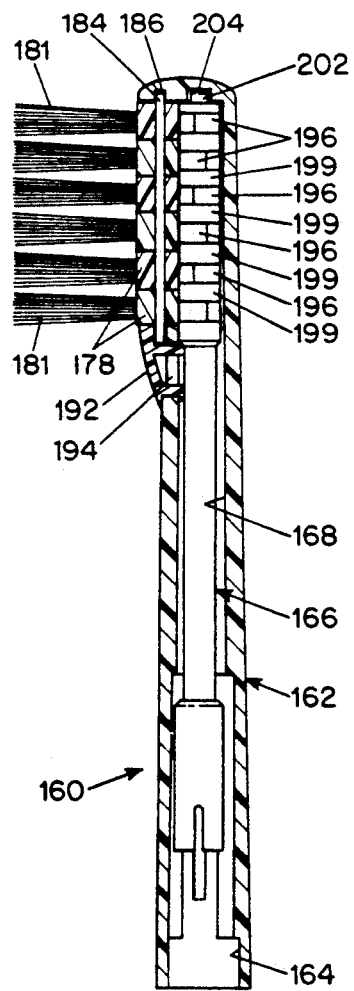
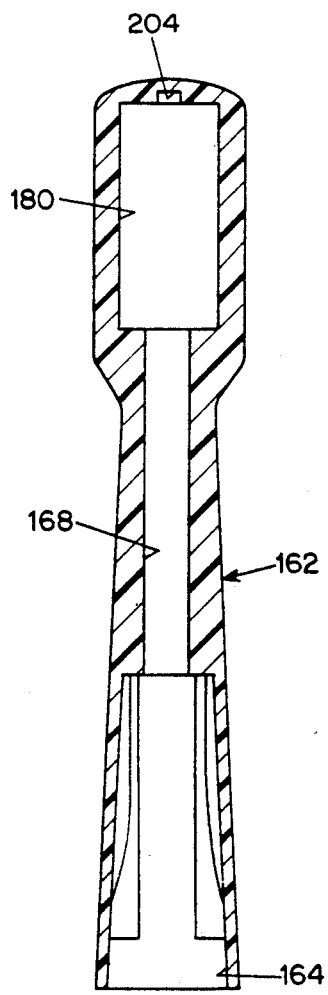
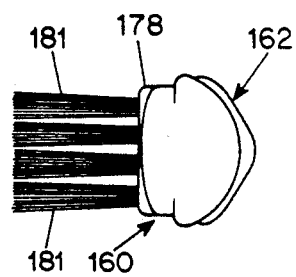
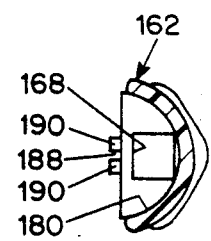
FIG. 4　　　FIG. 5　　　FIG. 8　　　FIG. 9

MOTOR-DRIVEN TOOTHBRUSH

FIELD OF THE INVENTION

The present invention relates to a motor-driven toothbrush and, in particular, a motor-driven toothbrush in which the bristles and, at the option of the user, the brush head carrying the bristles are moved relative to a hand-holdable drive unit.

BACKGROUND OF THE INVENTION

Motor-driven toothbrushes have been proposed and marketed commercially for many years, especially since long-lived rechargeable batteries and miniature electric motors have been available. A common form of motor-driven toothbrush comprises a hand-holdable drive unit and a brush unit that is pivoted about its axis relative to the drive unit by a motor-driven transmission, and thereby pivots the brushes as a unit from side-to-side so that they brush generally up and down on the teeth. In another known form a brush unit is reciprocated axially by a drive unit such that the brush moves generally from side to side across the teeth. A motor-driven toothbrush that allows the user to switch between a side-to-side pivot motion and an axial reciprocating motion of the brush head is currently being marketed. Also available is a motor-driven toothbrush in which a single, relatively large tuft of bristles is rotated unidirectionally about an axis parallel to the bristles in a manner similar to that of a cleaning brush used in a dentist's drill head by dental hygienists in cleaning teeth.

The motor driven toothbrush described and shown in U.S. Pat. No. 4,156,620 (Clemens, May 29, 1979) has a brush head carrying several bristle tufts, each of which is mounted to rotate about its lengthwise axis on a tiny spindle having a pinion gear. The bristle tufts are arranged in two ranks, one on each side of the longitudinal axis of the brush head, and the gears of the spindles of each rank mesh to form a train. Every other spindle in each rank is offset laterally from the remaining spindles. A motor in a hand-holdable drive unit drives through a gear transmission a crank arm that is linked to a longitudinally movable drive shaft extending through the brush head and having a rack gear on its end portion that meshes with the pinion gears on alternate ones of the bristle-mounting spindles in each rank. As the drive shaft reciprocates, the driven bristle tufts are rotated, first in one direction and then the other. The remaining bristle tufts are rotated in opposite directions to the driven ones due to the intermeshing of the gears in each rank. A motor-driven toothbrush of the type described and shown in the Clemens patent is widely sold.

Previously known motor-driven toothbrushes of the type in which the entire brush unit is moved relative to the drive unit in either rotational or axial reciprocation have several disadvantages. The bristle tufts, which are arranged in crosswise and lengthwise rows, move along straight tracks either up and down or crosswise over the teeth with gaps between the tracks. Therefore, thorough cleaning requires that the user move the device over the teeth to cover all areas, lest areas of the teeth not be cleaned where the gaps between the tuft rows are. The reactive forces to the brush movements are transmitted to the drive unit and by the brush unit to the user's hand, and some people do not like the vibration felt by the hand. Similarly, the back of the brush head often contacts and vibrates the lips and the tissues in the mouth, which can also be unpleasant for some users.

The longitudinally reciprocating types of brushes move exclusively across the teeth, and the bristles tend to move past the spaces between the teeth. Massaging of the gums is important to good dental hygiene, but the solely linear movements of the bristles do not produce a thorough massaging action for stimulation of blood circulation and tissue toning.

As far as cleaning the teeth is concerned, the individual rotating tufts of the Clemens patent type toothbrush do an excellent job. Because the individual tufts move very little transversely relative to their axes, however, the gum-massaging action is limited. The single rotating bristle tuft toothbrush requires considerable attention by the user to full coverage of the teeth and also fails to massage the gum tissues effectively.

SUMMARY OF THE INVENTION

One object of the present invention is to provide a motor-driven toothbrush that not only cleans the teeth extremely well but massages the gums in a unique and highly effective way. Another object is to reduce the vibration of the drive unit due to reactive forces imposed on it by the brush unit. Still another object is to provide two modes of brush action that can be chosen by the user to suit best his or her brushing preference. Advantageously, the user may brush with one mode and then go over the teeth again in the other mode. In one mode, the back of the brush head is not moved by the drive, which eliminates the vibrating contact with the lips and the tissues of the mouth.

Like the previously-known motor-driven toothbrush of the Clemens patent mentioned above, the toothbrush of the present invention has a drive unit that includes a motor and a transmission driven by the motor, the motor and transmission being received in a hand-holdable casing, and a brush unit that includes an elongated brush head arranged to be coupled at one end to the drive unit and a multiplicity of bristle holders movably mounted adjacent the other end of the brush head, each bristle holder having bristles affixed to it. A drive shaft couples the transmission to the bristle holders to impart movement to them relative to the brush head.

The present invention is characterized in that the transmission includes an output drive gear rotatable about an axis substantially coincident with the axis of the brush head, the drive shaft is coupled to the output drive gear so as to be driven in rotation thereby, the bristle holders are pivotably mounted individually on the brush head for rotation about a common mounting axis parallel to and spaced apart from the drive shaft axis, and each bristle holder is coupled to the drive shaft by a crank pin so that oscillatory pivotal motion is imparted separately to each holder about the mounting axis.

In preferred embodiments of the invention each of the bristle holders has a mounting hole, and a mounting pin is affixed to the brush head and is received through the holes in the bristle holders. A crankshaft coupled to the drive shaft has a crank pin for each bristle holder, and a crank pin follower portion on each bristle holder spaced apart from the mounting axis receives a corresponding crank pin. The crank pins for some of the bristle holders are circumferentially spaced apart from the crank pins for others of the bristle holders. For example, axially adjacent crank pins on the crankshaft may be circumferentially spaced apart by 180° of arc such that the oscillations of adjacent brush holders are 180° out of phase. Adjacent pairs of crank pins on the crankshaft are connected by crank arms having shoulders that engage surfaces of adjacent bristle holders such as to retain the bristle holders in axially closely-spaced positions on the crankshaft, the surfaces of the bristle holders engaged by the crank arms preferably being recesses in opposite side walls of the bristle holders. Advantageously, the crank pin follower portion of each bristle holder is a notch opening in an edge of the holder opposite from an edge from which the bristles extend, which facilitates assembly of the brush unit.

The brush head has at the brush end a cavity forming an opening in a side wall. The bristle holders are identical plate-like members received side by side in closely spaced relation in the cavity, each bristle holder carrying along an edge facing outwardly from the cavity a row of several bristle tufts. The mounting pin extends lengthwise of the brush head across the cavity opening and is fastened to the brush head. The crankshaft extends lengthwise of the brush head into the cavity on the opposite side of the mounting pin from the cavity opening. The edges of the bristle holder from which the bristle tufts extend are substantially contiguous to an imaginary surface bounded by the edge of the cavity opening.

In preferred embodiments, furthermore, the brush unit is detachably coupled to the drive unit so that the drive unit can be used interchangeably with numerous brush units. The crankshaft is arranged to be detachably coupled to the drive shaft axially and rotationally. The drive unit includes a brush head extension having a portion protruding from the casing, and a socket portion of the brush head is received on the end of the protruding portion in telescoping relation.

As an optional but highly desirable further characteristic of the invention, the transmission includes an output member movable back and forth in a direction lengthwise of the drive shaft, and the brush head is coupled to the output member such that it is driven lengthwise back and forth relative to the drive unit simultaneously with the side-to-side oscillation of the bristle holders relative to the drive unit. The output member is a member supported in the casing of the drive unit for reciprocating linear motion parallel to the axis of the drive shaft and having spaced-apart parallel cam follower surfaces disposed perpendicularly to the axis of the drive shaft, and the transmission includes a cam rotatable about an axis perpendicular to the drive shaft axis and parallel to the cam follower surfaces and having a cam surface that is eccentric to its axis of rotation and engages the cam follower surfaces. In particular, the output member may be a brush head extension having a portion protruding from the casing of the drive unit, and the brush unit is arranged to be detachably coupled to the brush head extension. The casing has an end cap having an opening defined by a guide flange that slidably supports the brush head extension for reciprocating motion. The drive shaft is coupled to the output drive gear of the transmission for rotation therewith and axial motion with the brush head extension relative thereto. The crankshaft of the brush unit is detachably coupled to the drive shaft.

Optionally, though preferably, the cam consists of an inner part having a circular cylindrical outer surface eccentric to its axis of rotation and an outer part received for rotation through a predetermined arc about the outer surface of the inner part, the cam surface being on the outer part and being eccentric to the outer surface of the inner part. When the cam is driven in rotation in one direction, the stroke of the output member is different from its stroke when the cam is driven in the opposite direction. The motor and battery are electrically connected through a switch operable to reverse the driving direction of the motor.

The cam that drives the brush head extension may be a portion of a crown gear, and the output drive gear and the crown gear are driven by a single pinion gear. The motor has a motor gear affixed to its shaft, and the pinion gear is coupled to the motor gear by a speed reduction gear train, for example, a planetary gear train having planet gears carried on shafts on a rotatable planetary gear carrier and meshing with the motor gear and with a stationary ring gear. The pinion gear is affixed to the planetary gear carrier.

A motor driven toothbrush according to the present invention is used by holding it with the brush head oriented generally crosswise of the teeth so that the laterally oscillating bristle tufts move generally vertically on the teeth. When operated in the combined-motion mode, in which the brush head reciprocates lengthwise as the bristle tufts oscillate laterally, the front and back surfaces of the teeth are cleaned very effectively by the combined crosswise and vertical movements of the bristles. In a preferred design, the frequency of the lateral oscillation is at least about twice the frequency of the lengthwise reciprocation, which causes the bristle tufts to move in a sideways figure "8" pattern. Also preferably, adjacent bristle holders oscillate laterally 180° out of phase, so that the directions of the figure "8" patterns of the tufts of adjacent holders are opposite. It is believed that the out-of-phase figure "8" patterns are very effective in massaging the gums by working the tissues on a relatively fine scale omnidirectionally.

The lengthwise motion of the brush head ensures good lateral coverage of the teeth, while the lateral motions of the bristle tufts dislodge debris and plaque by working vertically, the cleaning effect being especially desirable at the gum line due to the vertical components of the tuft movements that work the bristles perpendicularly against the gum line area. Cleaning at the gumline appears to be enhanced by the out-of-phase lateral oscillations of the bristle tufts; while the tufts of alternate holders push the gum up, thereby exposing the teeth at the gumline, the tufts of the remaining holders move down and remove plaque and debris. The crosswise (relative to the teeth) components of the tuft movements aid in working the bristles against the gumline by sliding them along the gumline simultaneously with moving them toward or away from the gumline. It is these same complex, simultaneous omni-directional motions that promote blood circulation by pushing and pulling the gum tissue in many directions between adjacent tufts that are moving in opposite directions, in all directions and out of phase.

Following brushing in the combined-motion mode, it is desirable to go over the teeth again with the toothbrush operated in the single-motion mode (lateral tuft movements only), which will cleanse the spaces between the teeth by working the tufts solely vertically for better penetration between the teeth.

When the motor-driven toothbrush of the present invention is operated without lengthwise reciprocation of the brush unit, the brush head is not moved by the drive unit and does not vibrate the lips or mouth tissues when it touches them. With 180° out-of-phase timing of the bristle holders, the reaction forces of lateral movements of the bristle tufts against the teeth are balanced, and no reaction forces are transmitted to the drive unit, which, therefore, is not subject to vibration.

For a better understanding of the invention, reference may be made to the following description of an exemplary embodiment and to the accompanying drawings of the embodiment.

DESCRIPTION OF THE DRAWINGS

FIG. 3 is a top plan view of the drive unit;

FIG. 4 is a side cross-sectional view of the brush unit of the embodiment;

FIG. 5 is a front cross-sectional view of the brush head;

FIG. 6 is a front view of the brush end of the brush head;

FIG. 7 is a side elevational view of the brush end of the brush head;

FIG. 8 is an end elevational view of the brush end of the brush head;

FIG. 9 is an end cross-sectional view of the brush head taken along the lines 9—9 of FIG. 7;

DESCRIPTION OF THE EMBODIMENT

Figure 1:
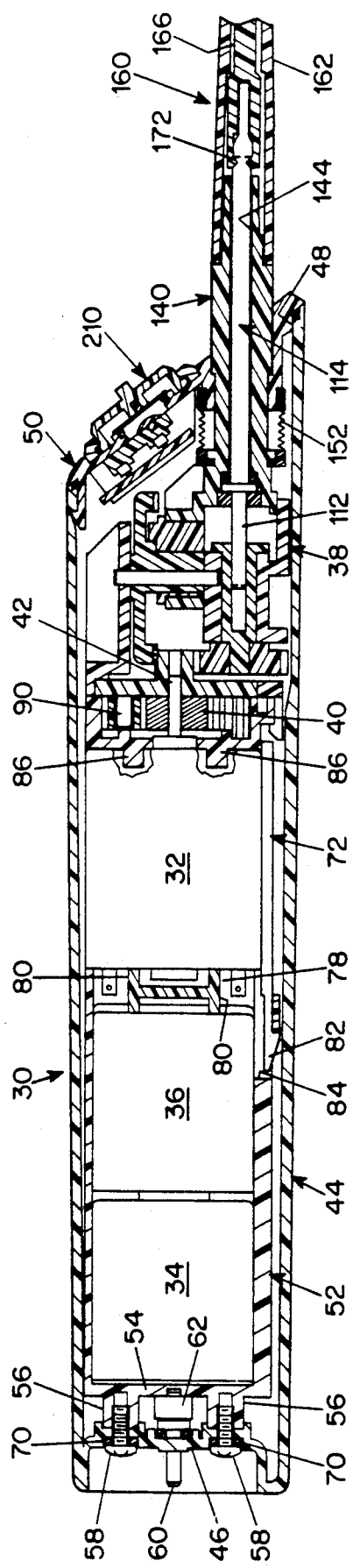
FIG. 1 is a side cross-sectional view of the drive unit of the embodiment.
Figure 2:
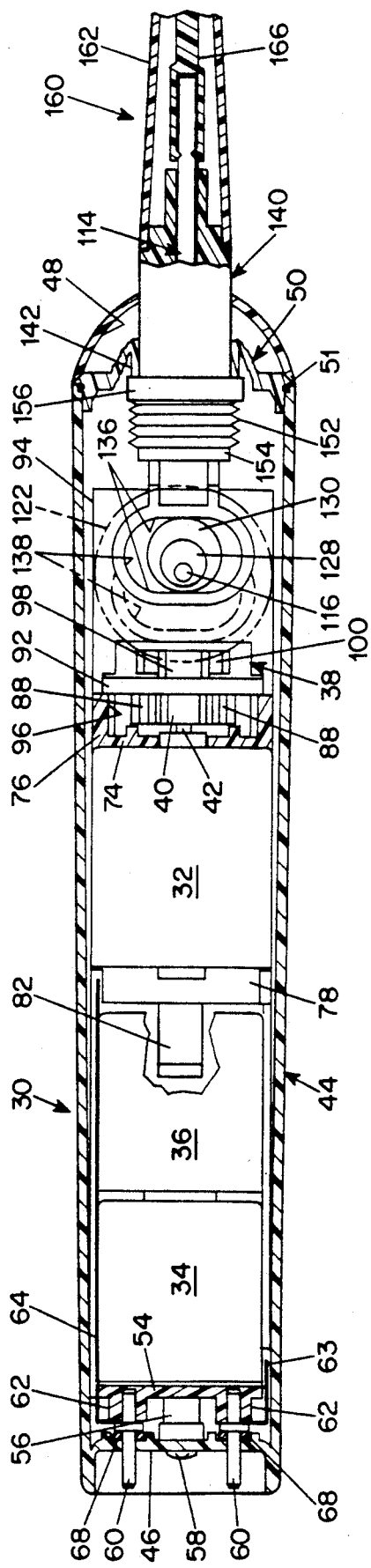
FIG. 2 is a front view of the drive unit with the casing broken away.

The drive unit 30 (FIGS. 1 to 3 and 21) comprises a miniature D.C. electric motor 32 that is powered by two rechargeable batteries 34, 36 and drives a transmission 38 through a motor gear 40 affixed to the motor shaft 42. The batteries, motor and transmission are housed within a casing 44 having an integral end wall 46 at the bottom end and an opening 48 at the other end that receives a cap 50, which is sealed to the casing by a sealing ring 51.

The batteries 34, 36 are received in a generally tubular battery holder 52. An end wall 54 of the holder 52 has two screw bosses 56 that receive screws 58 inserted through the end wall 46 of the casing 44 for securing the battery holder to the casing. Two electrical contact pins 60 are received in bosses 62 on the battery holder and protrude through the casing end wall 46. The contact pins mate with a receptacle in a charger/holder (not shown) for the drive unit. The drive unit is stored upright in the charger/holder when not in use, and while so stored, the batteries are recharged. The positive terminal of the battery 34 is soldered to an electrical lead 63 (a bent metal band, FIG. 2) having a hole that receives one of the pins 60. Another metal band lead 64 connects the negative terminal of the battery 36 to the other pin 60. The batteries 34, 36 are, of course, in end-to-end electrical contact in series. A diode 234 (see FIG. 22), which is physically located at the negative end of the battery 36 nearest the motor 32, is interposed in the electrical circuit between the negative terminal of the battery 36 and the negative contact pin 60 for the charger/holder. The contact pins 60 and the screws 58 are individually sealed to the casing end wall 46 by sealing rings 68 and 70 to prevent water from entering the casing.

The motor 32 is received in a cage-like motor holder 72 that includes a transverse end wall portion 74 at the shaft end, an annular flange portion 76 extending from the wall portion 74 in a direction away from the motor and lengthwise strips (not shown) that extend lengthwise along diametrically opposite flat portions of the side walls of the motor case. A cross piece 78 is joined to the ends of the strips, such as by heat-staking lugs on the strips received through holes in the cross piece 78. Flanges 80 on the cross piece engage the end of the battery 36, thereby to serve as a spacer between the battery and the motor. The motor holder 72 is joined to the battery holder 52 by three circumferentially spaced-apart hook portions 82 that extend from the flange portion 76 along the sides of the motor 32 and snap into holes 84 in the battery holder 52. Rotational positioning and restraint of the motor are enhanced by bosses 86 that extend into screw holes in the motor casing. Three elastomeric foam pads (not shown), approximately equally spaced apart circumferentially, are interposed between the flange portion 76 of the motor holder 72 and the wall of the casing 44 to provide vibration and noise isolation of the motor and transmission from the casing.

Figure 21:
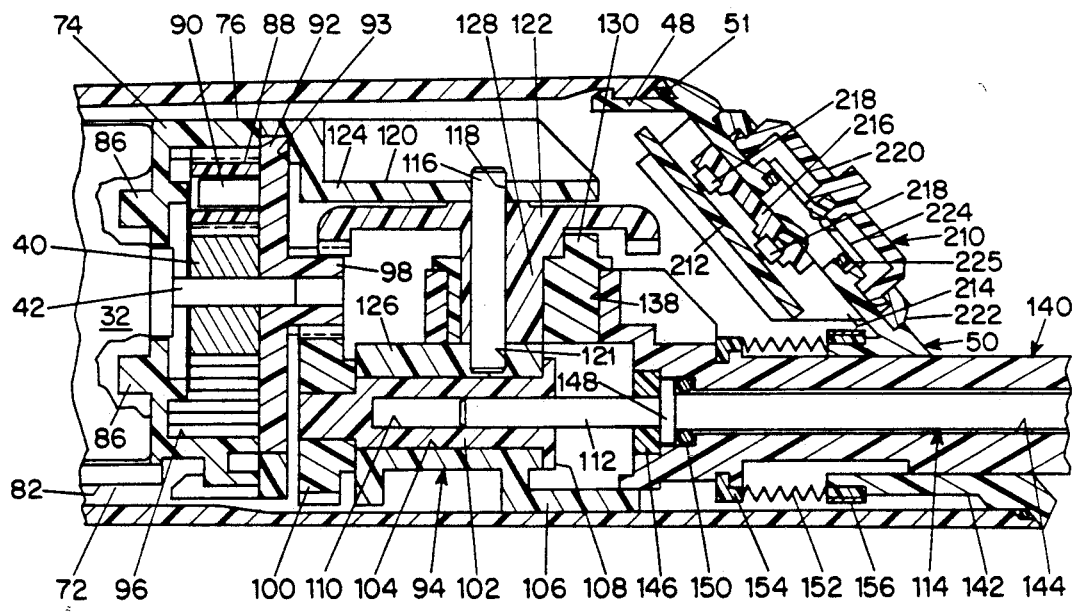
FIG. 21 is a detail side cross-sectional view of the transmission and the control switch on a larger scale than that of FIG. 1.

Each of three circumferentially spaced-apart planetary gears 88 (only one is shown in FIGS. 1 and 21 and only one is required) is received on a corresponding shaft 90 of a planetary gear carrier 92 that is received with a rotationally sliding fit between the distal end of the flange portion 76 of the motor holder and a shoulder 93 on a two-part gear housing 94. The planetary gears 88 are elements of a planetary gear train in which the motor gear 40 is the sun gear and the ring gear 96 is formed on the inner surface of the flange portion 76 of the motor casing. The sun gear (motor gear 40) drives the planetary gears 88, which react against the stationary ring gear 96 and thereby orbit about the sun gear and impart rotation to the planetary gear carrier 92 at a rotational speed (in rpm) substantially less than that of the motor shaft.

A pinion gear portion 98 of the carrier 92 meshes with and drives a drive gear 100 that is affixed to a drive shaft coupling 102. The drive shaft coupling 102 is rotatably received in a sleeve 104 in a lower part 106 of the gear housing 94 and is held axially in the sleeve by the face of the gear 100 at one end and a flange portion 108 at the other end. An axial hole 110 of square or other non-round cross-sectional shape in the drive shaft coupling 102 receives with a sliding fit a correspondingly shaped end portion 112 of a drive shaft 114.

Figure 19:
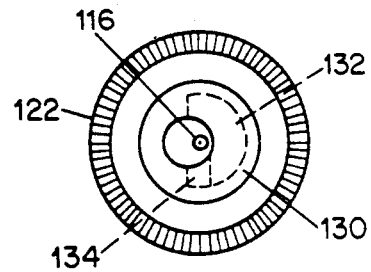
FIGS. 19 and 20 are plan views of the crown gear and the cam insert showing the two rotational positions of the cam insert relative to the crown gear, depending upon the direction of rotation of the crown gear.
Figures 16, 18:
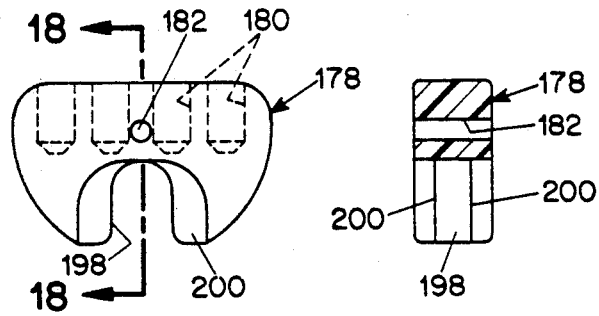
FIG. 18 is a side cross-sectional view of the brush holder taken along the lines 18—18 of FIG. 16.
Figure 17:
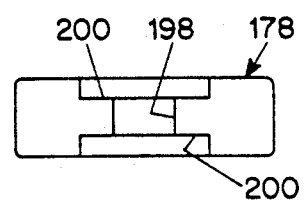
Figure 20:
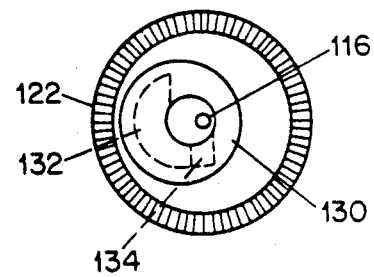

A shaft 116, the axis of which intersects the axis of the motor shaft and the gear 98 at a right angle, is mounted for rotation in an upper receiving socket 118 in an upper part 120 of the gear housing 94 and a lower receiving socket 121 in the lower gear housing part 106. A crown gear 122 press fitted on the shaft 116 is held in mesh with the pinion gear 98 of the planetary gear carrier by being captured axially of the shaft 116 between wall portions 124 and 126 of the gear housing 94. An integral eccentric drum cam boss 128 on the crown gear receives an eccentric drum cam insert 130. The cam insert 130 and crown gear 122 have abutments 132 and 134 that engage and restrict rotation of the cam insert to 180° relative to the cam boss. When the crown gear is driven in one direction by the pinion gear 98, the external cam surface of the cam insert is eccentric to the crown gear shaft 116 (see FIGS. 2 and 20), and when it is driven in the other direction (FIG. 19), the cam surface of the insert is concentric to the shaft 116.

The cam insert 130 works against the transversely extending, parallel walls 136 of a cam slot 138 in a brush head extension 140 that is slidably supported for movement along the axis of the drive shaft 114 within a guide flange portion 142 of the casing cap 50, with additional guiding support being contributed by slideways on the lower gear housing part 106 and the extension that restrict up and down motions of the cam slot. When the cam insert 128 is in its eccentric position relative to the crown gear 122, i.e., when the motor 32 drives the gear train formed by the planetary gear train, the gear 98 and the crown gear in one direction, the brush head extension is reciprocated axially relative to the casing. When the gear train is driven in the opposite direction such as to cause the cam insert 128 to stop in a position relative to the crown gear 122 in which its cam surface is concentric to the crown gear, the brush head extension 140 remains stationary relative to the drive unit 30.

The drive shaft 114 is rotatably received in a hole 144 extending lengthwise all the way through the brush head extension 140 and is fixed axially to the extension by a retainer bushing 146 that is heat-staked in place in a recess in the extension and engages a flange 148 on the drive shaft. An O-ring 150 seals the annulus between the drive shaft 114 and the extension 140. A flexible bellows seal 152 is attached by a flange 164 at one end to the extension 140 and clamped by a split band clamp 156 at its other end to the guide flange 142.

Figure 12:
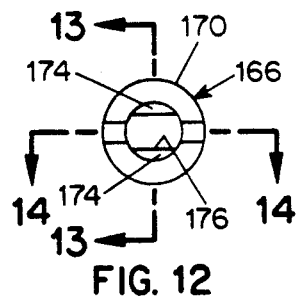
FIG. 12 is an end view of the coupling end of the crankshaft.
Figure 13:
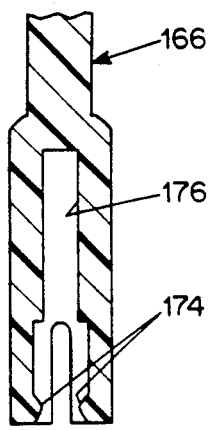
FIGS. 13 and 14 are side and top cross-sectional views of the coupling end of the crankshaft taken along the lines 13—13 and 14—14 of FIG. 12.
Figure 14:
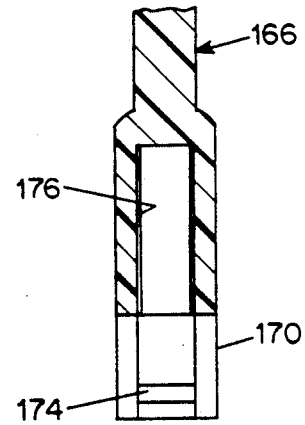
Figure 15:
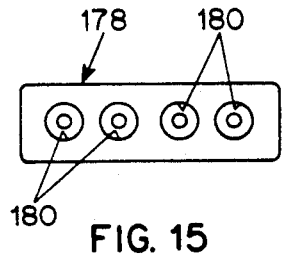
FIGS. 15 to 17 are a front view, a side view and a bottom view, respectively, of a bristle holder of the brush head.

A brush unit 160, which is shown in FIG. 4, is detachably coupled to the brush head extension 140 of the drive unit 30 so that a brush head for each member of a household can be interchanged and used with a single drive unit. A brush head 162 telescopically fits snugly by means of a socket portion 164 at one end onto the external end of the extension. A crankshaft 166 extends through a lengthwise hole 168 in the brush head and is coupled by a bifurcated coupling portion 170 (see FIGS. 12 to 14) to the external end of the drive shaft 114 of the drive unit. The drive shaft, which is metal for durability, has a groove 172 (see FIG. 1) that receives ribs 174 on the coupling portion 170 of the crankshaft. The tip of the drive shaft has diametrically opposite flat surfaces and fits into a socket portion 176 of the crankshaft that is of a corresponding cross-sectional shape (see FIG. 12), so that the drive shaft and crankshaft are rotationally fixed relative to each other.

Several identical bristle holders 178 (FIGS. 15 to 18)—six in the embodiment—are received in a cavity 180 in the head end of the brush head. Each holder 178 is a thin plate-like member having holes 180 along its outwardly facing edge that receive tufts 181 of bristles. A transverse hole 182 through each holder pivotably receives a mounting pin 184 (see FIG. 4), one end of which is captured in a hole 186 at one end of the cavity 180 of the brush head and the other end of which drops into a notch 188 formed by two tiny bosses 190 at the other end of the cavity. A pin retainer cap 192 snaps onto the brush head by means of hooks on the cap received in an opening 194 in the head. One of the hooks on the cap also captures the pin 184 lengthwise. The pin 184 defines a pivot axis for the bristle holders that is parallel to and spaced apart from the axis of the crankshaft 166.

Figure 10:
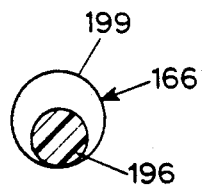
FIGS. 10 and 11 are end cross-sectional views of the brush unit crankshaft taken through longitudinally adjacent crank pins.
Figure 11:
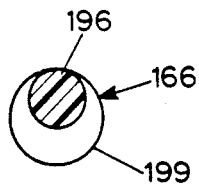

The crankshaft 166 has for each bristle holder 178 a crank pin 196 that is received in a follower portion 198 of the corresponding holder in the form of a notch having side walls parallel to each other and to a plane defined by the axis of the crankshaft 166 and the axis of the mounting pin 184. Each pin 196 is, of course, eccentric to the axis of the crankshaft and is joined to a crank arm 199 (see FIGS. 10 and 11). Preferably, but not indispensably, alternate crank pins are aligned on one side of the shaft axis while the remaining crank pins are aligned on the diametrically opposite side of the shaft axis. Upon rotation of the crankshaft adjacent bristle holders are pivoted about the pivot axis—the pin 184—from side to side in opposite directions, 180° out of phase, with this arrangement of the crank pins. The faces of the crank arms 199 adjacent the crank pins engage the faces of recesses 200 and hold the bristle holders 178 in closely adjacent positions in the cavity for proper tracking of the crank pins and for stabilizing the bristle holders against longitudinal cocking. A round boss 202 on the end of the crankshaft is received in a hole 204 in the end wall of the recess 180 of the brush head 162 to support as a bearing the crankshaft on its rotational axis transversely.

Figure 22:
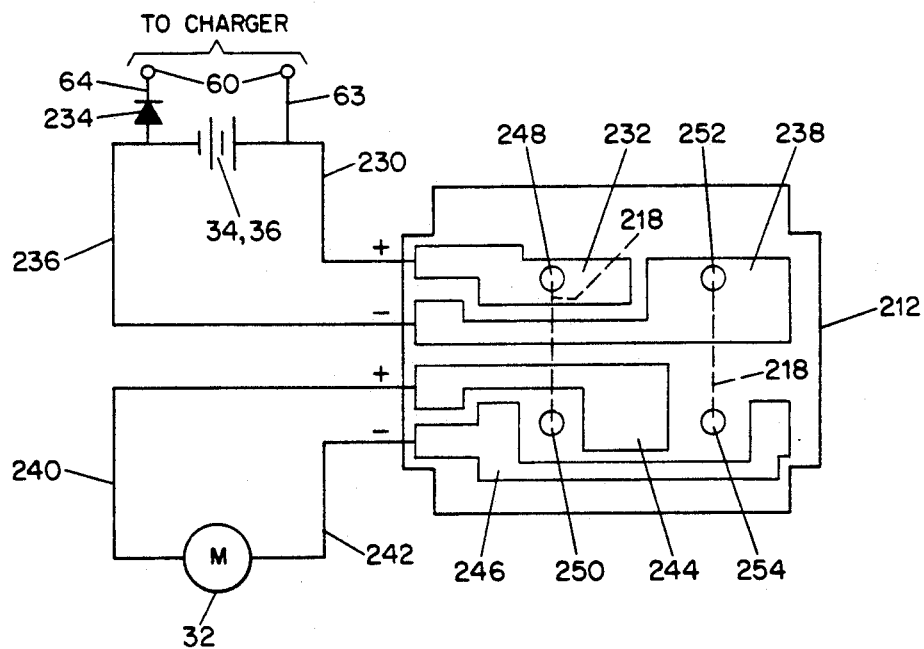
FIG. 22 is a diagram of the electrical circuit of the drive unit.

The motor 32 is turned on and off, and its direction of rotation is controlled, by a switch assembly 210 installed on the cap 50 (FIGS. 1 and 21). A printed circuit board 212 having contacts connected by wires to the motor and battery, as described below and shown in FIG. 22, is mounted on the inside of the cap 50 on a holder 214. A slider 216 having spring electrical contacts 218 bridging the contacts on the circuit board 212 is slidably supported by the holder. An operating knob 220 is rotatably mounted on the outside of the cap 50 by means of a retainer ring 222 and is coupled to a coupling disc 224 rotatably received in a round hole in the cap 50, with a sealing ring 225 interposed, by an eccentric pin on the disc 224 that is received in a slot on the underside of the knob 220 so that rotation of the knob correspondingly rotates the disc. Another eccentric pin on the other side (the inside) of the disc 224 runs in a transverse guideway on the slider, so that rotation of the disc causes translation of the slider so as to move the contacts to a selected one of three positions along the printed circuit board 212. Detents act between the slider and the holder to hold each switch position. Stop bosses on the cap 50 are engaged by ribs on the underside of the knob 220 to restrict rotation of the knob to that required to set the endmost two positions of the slider relative to the printed circuit board.

The printed circuit board 212 and a diagram of the electrical circuit of the drive unit 30 are shown in FIG. 22. The positive terminal of the series—paired batteries 34, 36 is connected by a wire 230 to a first conductor 232 of the circuit board and to one charger contact pin 60 by the conductor 63. The negative battery terminal is connected to the charger electrode pin 60 by the conductor 64 through a diode 234, which prevents reversal of the current flow through the battery in case the drive unit is plugged into an improper charger or forced, notwithstanding provisions for preventing improper orientation, into its charger/holder in a reversed position. The negative battery terminal is also connected by a wire 236 to a second circuit board conductor 238. The terminals of the motor 32 are connected by wires 240 and 242 to the respective circuit board conductors 244 and 246. In the drawing the circles 248 and 250 represent the contact points of one of the two spring contacts 218 on the slider 216, and the circles 252 and 254 represent the two contact points of the other spring contact on the slider.

The contact points of the spring contacts are shown in FIG. 22 in the off position of the switch assembly 210—the contact points 250 and 254 are in contact with non-conductive zones of the circuit board 212, so no current flows to the motor. Rotation of the knob 220 counterclockwise (with respect to FIG. 22) slides the slider to the left and brings contact points 250 and 254 onto the circuit board conductors 246 and 244, respectively, thereby completing the following circuit path between the battery terminals: battery positive, wire 230, conductor 232, spring contact points 248 and 250, conductor 246, wire 242, motor 32, wire 240, conductor 244, spring contact points 254 and 252, conductor 238, wire 236, battery negative. Rotation of the switch knob clockwise from the "off" position of the switch shown in FIG. 22 slides the slider 216 to the right and completes the following circuit path between the battery terminals: battery positive, wire 230, conductor 232, spring contact points 248, 250, contact 244, wire 240, motor 32, wire 242, conductor 246, contact points 254 and 252, conductor 238, wire 236 and battery negative. In the left position of the slider, the current flow through the motor 36 is reversed from what it is when the slider is in the right position.

It will be recalled that when the crown gear 122 is rotated in one direction, the cam surface of the cam insert 130 is concentric to the axis of the crown gear and the brush head extension 140 remains stationary, whereas when the crown gear is driven in the other direction, the cam surface of the cam insert 130 is eccentric to the crown gear axis and drives the brush head extension back and forth lengthwise. By selecting one of the two "on" positions of the switch 210, the user can operate the electric toothbrush in a mode in which the brush unit reciprocates lengthwise relative to the drive unit such as to move the bristles from side to side across the teeth or in a mode in which the brush unit remains stationary relative to the drive unit. In both modes, however, the bristles carried by each bristle holder pivot transversely, alternate ones pivoting in a direction opposite to the others 180° out of phase.

Preferably, though not essentially, the gear train for pivoting the bristles laterally and the gear train for moving the brush unit lengthwise are designed such that the frequency of lengthwise oscillation of the brush unit is considerably less than the frequency of lateral pivoting of the bristle holders; for example, a ratio of lengthwise frequency to lateral frequency of about one-half or less is desirable. As discussed above, such a relationship provides motions of the bristle tufts over the teeth in sideways figure "8" patterns, which clean the teeth very effectively and massage the gums in an especially advantageous manner, involving fine-scale omnidirectional bristle motions. Desirable frequencies for the brush motions are of the order of 1000 cycles per minute for the lateral movements of the holders and of the order of 500 cycles per minute for the lengthwise movement of the brush head. The brush head lengthwise stroke distance is preferably about 5.0 to 6.0 mm., and the lateral excursions of the bristle tufts about 3.0 to 4.0 mm.

The provision of separate bristle holders facilitates the provision of bristles of different stiffnesses or materials, if desired. The bristles of the individual bristle holders of the group can be inserted in separate tuft-inserting machines set up to run different bristles. For example, the endmost two holders may have stiffer bristles than the remaining four, the endmost two holders being fitted with bristles in a different machine from that used for the other four holders (or the same machine set up for separate runs of the different bristles).

I claim:

1. A motor-driven toothbrush having a drive unit that includes a motor and a transmission driven by the motor received in a hand-holdable casing; a brush unit that includes an elongated brush head arranged to be coupled at one end to the drive unit and a multiplicity of bristle holders movably mounted adjacent the other end of the brush head, each bristle holder having bristles affixed to it; and a drive shaft coupling the transmission to the bristle holders to impart movement to them relative to the brush head; characterized in that the transmission includes an output drive gear rotatable about an axis substantially coincident with the axis of the brush head, the drive shaft is coupled to the output drive gear so as to be driven in rotation thereby, the bristle holders are pivotably mounted individually on the brush head for rotation about a common mounting axis parallel to and spaced apart from the drive shaft axis, and each bristle holder is coupled to the drive shaft by crank means for imparting oscillatory pivotal motion to each holder individually about the mounting axis.

2. A motor-driven toothbrush according to claim 1 and further characterized in that each of the bristle holders has a mounting hole, and a mounting pin is affixed to the brush head and is received through the holes in the bristle holders.

3. A motor-driven toothbrush according to claim 2 and further characterized in that the crank means includes a crankshaft having a crank pin for each bristle holder and a crank pin follower portion on each bristle holder spaced apart from the mounting axis and receiving a corresponding crank pin.

4. A motor-driven toothbrush according to claim 3 and further characterized in that the crank pins for some of the bristle holders are circumferentially spaced apart from the crank pins for others of the bristle holders.

5. A motor-driven toothbrush according to claim 4 and further characterized in that axially adjacent crank pins are circumferentially spaced apart by 180° of arc such that the oscillations of adjacent brush holders are 180° out of phase.

6. A motor-driven toothbrush according to claim 4 and further characterized in that adjacent pairs of crank pins are connected by crank arms having shoulders that engage surfaces of adjacent bristle holders such as to retain the bristle holders in axially closely-spaced positions on the crankshaft.

7. A motor-driven toothbrush according to claim 6 and further characterized in that the surfaces of the bristle holders engaged by the crank arms are recesses in opposite side walls of the bristle holders.

8. A motor-driven toothbrush according to claim 3 and further characterized in that the crank pin follower portion of each bristle holder is a notch opening in an edge of the holder opposite from an edge from which the bristles protrude.

9. A motor-driven toothbrush according to claim 1 and further characterized in that the brush head has adjacent its end remote from the drive unit a cavity forming an opening in a side wall, the bristle holders are identical plate-like members received side by side in closely spaced relation in the cavity, each bristle holder carries along an edge facing outwardly from the cavity a row of several bristle tufts, a mounting pin extends lengthwise of the brush head across the cavity opening and is fastened to the brush head, each bristle holder has a hole pivotably receiving the mounting pin, a crankshaft extends lengthwise of the brush head into the cavity on the opposite side of the mounting pin from the cavity opening, and a crank pin on the crankshaft engages crank pin follower surfaces on each bristle holder.

10. A motor-driven toothbrush according to claim 9 and further characterized in that the edges of the bristle holders from which the bristle tufts extend are substantially contiguous to an imaginary surface bounded by the edge of the cavity opening.

11. A motor-driven toothbrush according to claim 1 and further characterized in that the brush unit is detachably coupled to the drive unit.

12. A motor-driven toothbrush according to claim 11 and further characterized in that the crank means includes a crankshaft rotatably received in the brush head and coupled to the bristle holders and there are detachable coupling means on the drive shaft and the crankshaft for joining them together axially and rotationally.

13. A motor-driven toothbrush according to claim 11 and further characterized in that the drive unit includes a brush head extension having a portion protruding from the casing and a portion of the brush head is received in the end of the protruding portion in telescoping relation.

14. A motor-driven toothbrush according to claim 1 and further characterized in that the transmission includes an output member movable in a direction lengthwise of the drive shaft and the brush head is coupled to the output member such that it is driven lengthwise back and forth relative to the drive unit simultaneously with the side-to-side oscillations of the bristle holders relative to the drive unit.

15. A motor-driven toothbrush according to claim 14 and further characterized in that at least a portion of the drive shaft that is coupled to the bristle holders is movable longitudinally with the brush head relative to the output drive gear of the transmission.

16. A motor-driven toothbrush according to claim 15 and further characterized in that the output member is a member that is supported in the casing of the drive unit for reciprocating linear motion parallel to the axis of the drive shaft and has spaced-apart parallel cam follower surfaces disposed perpendicularly to the axis of the drive shaft and the transmission includes a cam rotatable about an axis perpendicular to the drive shaft axis and parallel to the cam follower surfaces and having a cam surface disposed eccentrically to its axis of rotation and engaging the cam follower surfaces.

17. A motor-driven toothbrush according to claim 16 and further characterized in that the cam consists of an inner part having a circular cylindrical outer surface eccentric to its axis of rotation and an outer part received for rotation through a predetermined arc about the outer surface of the inner part, the cam surface being on the outer part and being eccentric to the outer surface of the inner part, whereby when the cam is driven in rotation in one direction the stroke of the output member is different from its stroke when the cam is driven in the opposite direction.

18. A motor-driven toothbrush according to claim 17 and further characterized in that the motor is electrically connected to a power source through a switch operable to reverse the driving direction of the motor.

19. A motor-driven toothbrush according to claim 16 and further characterized in that the cam is a portion of a crown gear and the output drive gear and the crown gear are driven by a single pinion gear.

20. A motor-driven toothbrush according to claim 19 and further characterized in that the motor has a motor gear affixed to its shaft, and the pinion gear is coupled to the motor gear by a speed reduction gear train.

21. A motor-driven toothbrush according to claim 20 and further characterized in that the speed reduction gear train is a planetary gear train having planet gears carried on shafts on a rotatable planetary gear carrier and meshing with the motor gear and with a stationary ring gear, and the pinion gear is affixed to the planetary gear carrier.

22. A motor-driven toothbrush according to claim 15 and further characterized in that the output member is a brush head extension having a portion protruding from the casing of the drive unit, and the brush unit is detachably coupled to the brush head extension.

23. A motor-driven toothbrush according to claim 22 and further characterized in that the casing has an end cap having an opening defined by a guide flange that slidably supports the brush head extension for reciprocating lengthwise motion.

24. A motor-driven toothbrush according to claim 22 and further characterized in that the drive shaft is coupled to an output drive gear of the transmission for rotation therewith and for axial motion with the brush head extension relative to the output drive gear, and a crankshaft is detachably coupled to the drive shaft for rotation and axial movement therewith.

* * * * *